United States Patent
Duffield et al.

(10) Patent No.: US 12,042,493 B2
(45) Date of Patent: Jul. 23, 2024

(54) PHARMACEUTICAL COMPOUNDS FOR USE IN TREATING HUNTINGTON'S DISEASE

(71) Applicant: ADEPTIO PHARMACEUTICALS LIMITED, London (GB)

(72) Inventors: Andrew John Duffield, London (GB); Anant Pandya, London (GB)

(73) Assignee: ADEPTIO PHARMACEUTICALS LIMITED, London (GB)

( * ) Notice: Subject to any disclaimer, the term of this patent is extended or adjusted under 35 U.S.C. 154(b) by 812 days.

(21) Appl. No.: 17/054,261

(22) PCT Filed: May 22, 2019

(86) PCT No.: PCT/EP2019/063253
§ 371 (c)(1),
(2) Date: Nov. 10, 2020

(87) PCT Pub. No.: WO2019/224269
PCT Pub. Date: Nov. 28, 2019

(65) Prior Publication Data
US 2021/0236479 A1    Aug. 5, 2021

(30) Foreign Application Priority Data
May 23, 2018 (GB) .................................. 1808464

(51) Int. Cl.
A61K 31/4745    (2006.01)
A61P 25/14    (2006.01)

(52) U.S. Cl.
CPC .......... *A61K 31/4745* (2013.01); *A61P 25/14* (2018.01)

(58) Field of Classification Search
None
See application file for complete search history.

(56) References Cited

U.S. PATENT DOCUMENTS

| | | | |
|---|---|---|---|
| 7,919,622 B2 | 4/2011 | Amarasinghe et al. | |
| 8,039,627 B2 | 10/2011 | Gano | |
| 10,660,885 B2 | 5/2020 | Duffield et al. | |
| 11,103,498 B2 * | 8/2021 | Duffield ............... | A61K 9/2846 |
| 2010/0087475 A1 | 4/2010 | Duffield et al. | |
| 2012/0003330 A1 | 1/2012 | Gant et al. | |
| 2017/0183346 A1 | 6/2017 | McGee et al. | |
| 2018/0280359 A1 | 10/2018 | Duffield et al. | |
| 2018/0280360 A1 | 10/2018 | Duffield et al. | |
| 2018/0280361 A1 | 10/2018 | Duffield et al. | |
| 2018/0280374 A1 | 10/2018 | Duffield et al. | |
| 2019/0111035 A1 | 4/2019 | Duffield et al. | |
| 2020/0246324 A1 | 8/2020 | Duffield et al. | |

FOREIGN PATENT DOCUMENTS

| | | |
|---|---|---|
| CN | 102285984 A | 12/2011 |
| GB | 800969 A | 9/1958 |
| GB | 2463452 A | 3/2010 |
| WO | 2005077946 A1 | 8/2005 |
| WO | 2006053067 A2 | 5/2006 |
| WO | 2007007105 A1 | 1/2007 |
| WO | 2007017654 A1 | 2/2007 |
| WO | 2008058261 A1 | 5/2008 |
| WO | 2009073677 A1 | 6/2009 |
| WO | 2010018408 A2 | 2/2010 |
| WO | 2010026436 A2 | 3/2010 |
| WO | 2011153157 A2 | 12/2011 |
| WO | 2014047167 A1 | 3/2014 |
| WO | 2015120110 A2 | 8/2015 |
| WO | 2015171802 A1 | 11/2015 |
| WO | 2016127133 A1 | 8/2016 |
| WO | 2016210180 A2 | 12/2016 |
| WO | 2017112857 A1 | 6/2017 |
| WO | 2018140092 A1 | 8/2018 |
| WO | 2018140093 A1 | 8/2018 |
| WO | 2018140094 A1 | 8/2018 |
| WO | 2018140095 A2 | 8/2018 |
| WO | 2018140096 A1 | 8/2018 |
| WO | 2018178243 A1 | 10/2018 |
| WO | 2018178251 A1 | 10/2018 |

OTHER PUBLICATIONS

Yao, et al., "Preparation and Evaluation of Tetrabenazine Enantiomers and All Eight Stereoisomers of Dihydrotetrabenazine as VMAT2 Inhibitors", Eur. J. Med. Chem., 46, pp. 1841-1848, (2011).

Kilbourn, et al., "Binding of α-dihydrotetrabenazine to the Vesicular Monoamine Transporter is Stereospecific", Eur. J. Pharmacol., 278(3), pp. 249-252, (1995).

(Continued)

*Primary Examiner* — Brian J Davis
(74) *Attorney, Agent, or Firm* — Heslin Rothenberg Farley & Mesiti P.C.

(57) ABSTRACT

The invention provides (+)-α-dihydrotetrabenazine or a pharmaceutically acceptable salt thereof for use in reducing the life-shortening effect of Huntington's Disease in mammals.

Also provided by the invention are (+)-α-dihydrotetrabenazine or a pharmaceutically acceptable salt thereof for use in preventing or delaying the onset of late stage Huntington's Disease; or for use in preventing or delaying the onset of life-threatening symptoms or events exhibited during late stage Huntington's disease.

12 Claims, 4 Drawing Sheets

(56) References Cited

OTHER PUBLICATIONS

Bhatnagar, et al., "Pharmacokinetics of Dihydrotetrabenazine After Intravenous and Peroral Administration to Rats", Pharm Pharmacol Lett, 2(3), pp. 89-91, (1992).
Mehvar, et al., "Pharmacokinetics of Tetrabenazine and its Major Metabolite in Man and Rat", Drug Metab. Dispos., 15(2), pp. 250-255, (1987).
Roberts, et al., "The Pharmacokinetics of Tetrabenazine and its Hydroxy Metabolite in Patients Treated for Involuntary Movement Disorders", Eur. J. Clin. Pharmacol., 29, pp. 703-708., (1986).
Kilbourn, et al., "Absolute Configuration of (+)-α-Dihydrotetrabenazine, an Active Metabolite of Tetrabenazine", Chirality, 9, pp. 59-62, (1997).
Brossi, et al., "Syntheseversuche in der Emetin-Reihe, 3. Mitteilung", Helv. Chim Acta., vol. XLI, No. 193, pp. 1793-1806, (1958) (and English Translation).
Schwartz, et al, "Metabolic Studies of Tetrabenazine, A Psychotropic Drug in Animals and Man", Biochem. Pharmacol., 15, pp. 645-655, (1956).
Scherman, et al., "Hydrophobicity of the Tetrabenazine-Binding Site of the Chromaffin Granule Monoamine Transporter", Mol. Pharmacol., 33, pp. 72-77, (1987).
Mehvar, et al., "Concentration-Effect Relationships of Tetrabenazine and Dihydrotetrabenazine in the Rat", J. Pharm. Sci., 76(6), pp. 461-465, (1987).
Kilbourn, et al., "PET Radioligands for Vesicular Neurotransmitter Transporters", Med. Chem. Res., 5, pp. 113-126, (1994).
Kilbourn, et al., "In Vivo Measures of Dopaminergic Radioligands in the Rat Brain: Equilibrium Infusion Studies", Synapse, 43, pp. 188-194, (2002).
Müller, "Valbenazine Granted Breakthrough Drug Status for Treating Tardive Dyskinesia", Expert Opin. Investig. Drugs, 24(6), pp. 737-742, (2015).
Hauser, et al., "KINECT 3: A Randomised, Double-Blind Placebo-Controlled Phase 3 Trial of Valbenazine (NBI-98854) for Tardive Dyskinesia (PL02.003)", Neurology, (2016), 86(16 Supplement). Abstract.
Hauser, et al., "KINECT 3: A Phase 3 Randomised, Double-Blind Placebo-Controlled Trial of Valbenazine for Tardive Dyskinesia", Am. J. Psychiatry, 174(5), pp. 476-484, (2017).
Ashcroft, et al., "A Comparison of Tetrabenazine and Chlorpromazine in Chronic Schizophrenia", Br. J. Psychiatry, 107(447), pp. 287-293, (1961).
Chen, et al., "Tetrabenazine for the Treatment of Hyperkinetic Movement Disorders: A Review of the Literature", Clin. Ther., 34(7), pp. 1487-1504, (2012).
Shen, et al., "Safety and Efficacy of Tetrabenazine and Use of Concomitant Medications During Long-Term, Open-Label Treatment of Chorea Associated with Huntington's and Other Diseases", Tremor Other Hyperkinet Mov, 3, pp. 1-13., (2013).
Skor, et al., "Differences in Dihydrotetrabenazine Isomer Concentrations Following Administration of Tetrabenazine and Valbenazine", Drugs R&D, 17(3), pp. 449-459, (2017).
"Archive History for NCT02844179 (+)-Alpha-Dihydrotetrabenazine Phase I" U.S. National Library of Medicine, https://clinicaltrials.gov/ct2/history/NCT02844179?V_1=View#StudyPageTop (2016).
Kilbourn, "Rat pancreas uptake of [11C]dihydrotetrabenazine stereoisomers" Nucl. Med. Biol. (2010), 37(8), pp. 869-871.
Boldt et al., "Synthesis of (+)- and (−) Tetrabenazine from the Resolution of [alpha]-Dihydrotetrabenazine", Synth. Commun., (2009), 39(20), pp. 3574-3585.
Walkup, J.T., "A Guide to Tourette Syndrome Medications", https://depts.washington.edu/dbpeds/A%20Guide%20to%20TS%20Medications_M-313.pdf, pp. 1-14 (2008).
International Search Report on PCT/EP2019/063253 mailed Sep. 20, 2019, 12 pp.
IPRP (Chapter II) on PCT/EP2019/063253 mailed May 11, 2020, 20 pp.
UKIPO Search Report on GB1808464.0 mailed Nov. 8, 2018, 5 pp.
Williams et al., "Comparative semi-automated analysis of (CAG) repeats in the Huntington disease gene: use of internal standard", Molecule and Cellular Probes, (1999), 13(4), pp. 283-289.

\* cited by examiner

PHARMACEUTICAL COMPOUNDS FOR USE IN TREATING HUNTINGTON'S DISEASE

CROSS REFERENCE TO RELATED APPLICATIONS

This application is a national stage filing under section 371 of International Application No. PCT/EP2019/063253, filed on May 22, 2019, and published on Nov. 28, 2019 as WO 2019/224269, which claims priority to Great Britain Application No. 1808464.0, filed on May 23, 2018. The entire contents of WO 2019/224269 are hereby incorporated herein by reference.

This invention relates to a (+)-dihydrotetrabenazine isomer (and in particular (+)-α-dihydrotetrabenazine) for use in reducing the life-shortening effect of Huntington's Disease in mammals.

BACKGROUND OF THE INVENTION

Huntington's Disease (HD), formerly known as Huntington's Chorea, is an inherited neuro-degenerative disease that is currently incurable. The disease is caused by an elongated CAG trinucleotide repeat expansion (referred to as HD mutation) in the IT15 gene located on the short arm of chromosome 4p16.3 which produces an abnormal form of a protein named Huntingtin. The abnormal protein triggers a process that results in the death of neurons in the corpus striatum region of the brain, possibly by the clumping or aggregation of the abnormal protein inside many types of neurons.

The IT15 gene, Huntingtin, comprises a segment of DNA which contains the repeating sequence of nucleotides CAG coding for the amino acid glutamine. It has been found that if there are thirty or fewer CAG repeats within the gene, a person carrying the gene will not contract HD. Typically, in non-sufferers the repeat is in the range of 6 to 26. However, persons carrying a gene in which there are over forty CAG repeats do tend to contract the disease. A longer CAG repeat generally results in an earlier onset of the disease, with 55 or more CAG repeats being common in Juvenile Huntington's disease. (Roos, "Huntington's disease: a clinical review", (2010), Orphanet Journal of Rare Diseases, 5(40)).

Huntington's disease is transmitted via an autosomal dominant inheritance pattern such that each child of an HD-affected parent has a 50% chance of inheriting the disorder. The symptoms of Huntington's disease typically appear between the ages of about 30 and 50 years and the disease usually progresses over a 10-25 year period. The characteristics and symptoms of the disease include personality changes, depression, mood swings, unsteady gait, involuntary chorea, twitching and jerking movements and tremors, dementia, slurred speech, impaired judgement, difficulty in swallowing and an intoxicated appearance.

Once an individual becomes symptomatic for Huntington's disease the course of the disease can last anywhere from ten to thirty years. Typically, the course of HD can be roughly divided into three stages, the early, middle and late stages.

In the early stage, patients can still perform most of their usual activities. They may still be working and may still be able to drive. Whilst they may exhibit slight uncontrollable movements, stumbling and clumsiness, lack of concentration, short-term memory lapses and depression, as well as mood swings, the involuntary movements are relatively mild, speech is still clear, and dementia, if present at all, is mild.

During the middle stage, patients become more disabled and typically need assistance with some of their routine daily activities. Falls, weight loss, and swallowing difficulties may be a problem during this stage and dementia becomes more obvious to the casual observer. In addition, the uncontrollable movements become more pronounced.

During the late stage, patients deteriorate to the point where they require almost total care and many require constant attention in hospitals or nursing homes. At this stage, they may no longer be able to walk or speak and, although they may show fewer involuntary movements, may become more rigid. Patients in this stage are often unable to swallow food. At this stage most patients lose insight and are apparently unaware of their surroundings. When the patient finally dies, the cause of death is usually related to the same natural causes that lead to death in other severely debilitated patients, such as malnutrition or pneumonia.

Patients suffering from Huntington's Disease tend to have a reduced lifespan. Although Huntington's Disease is not fatal in itself, sufferers tend to die from life-threatening complications associated with the diseases (Complications of Huntington's Disease, Stephanie Liou, 26 Jun, 2010 Lifestyle and HD). The most common cause of death is pneumonia, which accounts for approximately one third of deaths of those with Huntington's Disease. As the ability to synchronize movements deteriorates, a difficulty in clearing the lungs and an increased risk of aspirating food or drink both increase the risk of contracting pneumonia. The second greatest cause of death is heart disease, which causes almost a quarter of fatalities of those with the disease. (Walker, "Huntington's disease", Lancet, (2007), 369 (9557), pp. 218-228). Suicide is the third greatest cause of fatalities, with 7.3% of those with HD taking their own lives and up to 27% attempting to do so. It is unclear to what extent suicidal thoughts are influenced by behavioural symptoms or medication, as they signify sufferers' desires to avoid the later stages of the disease.

Additionally, HD patients have a higher incidence of choking and respiratory complications and gastrointestinal diseases (such as cancer of the pancreas) than the non-HD population.

According to the US National Institute of Neurological Disorders and Stroke (NINDS), a part of the National Institute of Health (NIH), there is currently no way of stopping or reversing the course of Huntington's disease.

Attempts have been made to develop treatments for HD and one study by Karpuj et al in Nature Medicine, February 2002, vol. 8, no.2, pp. 143-149 has involved the administration of cystamine. Apparently, the cystamine inactivates the enzyme transglutaminase which helps to create the clumps of Huntingtin protein thought to be responsible for the disease. Nevertheless, at present, so far as the applicants are aware, there is currently no generally available medicine for treating or arresting the progression of Huntington's disease. Although current treatments may reduce the incidence or severity of symptoms associated with the disease (such as tremors), these do not halt or retard the progression of the disease itself.

The discovery of the gene responsible for Huntington's disease (see the paper by the Huntington's Disease Collaborative Group, Cell, Vol. 72, Mar. 26, 1993, p. 971) has enabled diagnostic tests for the presence of the mutant form of the gene to be developed. Diagnostic tests, which make use of the polymerase chain reaction (PCR) to detect the number of CAG repeats on the IT-15 gene, are now widely available and allow a prediction to be made whether or not a patient will develop the symptoms of Huntington's disease; see for example the review by M. Hayden et al, Am. J. Hum. Genet. 55:606-617 (1994); the article by S. Hersch, "The Neurogenetics Genie: Testing for the Huntington's disease mutation." Neurol. 1994; 44:1369-1373; and the article by R. R. Brinkman et al. (1997) "The likelihood of being affected with Huntington disease by a particular age, for a specific CAG size", Am. J. Hum. Genet. 60:1202-1210.

The R6/1 and R6/2 transgenic mice were the first transgenic mouse models developed to study Huntington's Disease (Robert J. Ferrante, Biochim. Biophys. Acta., 2009, 506-520). Both forms express exon 1 of the human HD gene with around 115 and 150 CAG repeats, respectively. (Li et al., "The Use of the R6 Transgenic Mouse Models of Huntington's Disease in Attempts to Develop Novel Therapeutic Strategies." NeuroRx, (2005), 2(3), pp. 447-464.) The transgene expression in those mice is driven by the human huntingtin promoter and the resulting levels of transgene expression are around 31% and 75% of the endogenous huntingtin in the R6/1 and R6/2 models, respectively. The R6/2 mouse develops symptoms more rapidly than the R6/1 mouse and has a more widespread occurrence of huntingtin inclusions in the brain. Ferrante notes that recent findings suggest that the R6/2 HD model exhibits a progressive HD-like behavioural and neuropathological phenotype that more closely corresponds to human HD than previously believed and that the R6/2 model is an appropriate model for testing potential therapies for Huntington's Disease.

R6/2 mice display the initial signs of motor symptoms (e.g. locomotor hyperactivity) at approximately 3 weeks of age. Whilst the R6/2 mice are initially hyperactive, their motor activity gradually reduces such that they are hypoactive by around 8 weeks of age. By 8-12 weeks of age, the R6/2 mice are typically severely impaired. The R6/2 mice have a shortened lifespan compared to wild-type mice and have been variously reported as surviving to about 13-16 weeks of age (Li et al., ibid) or 14-21 weeks (Ferrante, idem), or up to 25 weeks (https://www.criver.com/products-services/discovery-services/vivo-pharmacology/rare-disease-pharmacology-models/vivo-models-huntingtons-disease/r62-mouse?region=3696) but with a mean lifespan of 105-120 days.

Tetrabenazine (Chemical name: 1,3,4,6,7,11b-hexahydro-9,10-dimethoxy-3-(2-methylpropyl)-2H-benzo(a)quinolizin-2-one) has been in use as a pharmaceutical drug since the late 1950s. Initially used as an anti-psychotic, tetrabenazine is currently used for treating hyperkinetic movement disorders including Huntington's disease, as well as hemiballismus, senile chorea, tic, tardive dyskinesia and Tourette's syndrome, see for example Jankovic et al., Am. J. Psychiatry. (1999) Aug; 156(8): 1279-81 and Jankovic et al., Neurology (1997) Feb; 48(2):358-62.

The primary pharmacological action of tetrabenazine is to reduce the supply of monoamines (e.g. dopamine, serotonin, and norepinephrine) in the central nervous system by inhibiting the human vesicular monoamine transporter isoform 2 (hVMAT2). The drug also blocks post-synaptic dopamine receptors.

The central effects of tetrabenazine closely resemble those of reserpine, but it differs from reserpine in that it lacks activity at the VMAT1 transporter. The lack of activity at the VMAT1 transporter means that tetrabenazine has less peripheral activity than reserpine and consequently does not produce VMAT1-related side effects such as hypotension.

Tetrabenazine was approved for the treatment of chorea associated with Huntington's Disease in 2001 (P. Diana, Neuropsychiatric Disease and Treatment, 2007: 3(5) 545-551) and has been marketed for the treatment of patients suffering from Huntington's disease since August 2008 under the trade name XENAZINE®. However, XENAZINE is only indicated for the treatment of chorea (https://www.accessdata.fda.gov/drugsatfda_docs/label/2008/021894lbl.pdf), i.e. the symptoms of the disease, and is not directed at the underlying causes of the disease. According to Diana, there is no treatment that can cure or slow the course of the disease and the available treatments are mostly focused on ameliorating depression, psychosis and chorea arising from HD.

More recently deutetrabenazine (a form of tetrabenazine wherein the six hydrogen atoms on the two methoxy groups are all replaced with deuterium) has also been approved for the treatment of chorea associated with Huntington's Disease. Wang et al., (Molecular Neurodegeneration 2010, 5:18 (http://www.molecular neurodegeneration. com/content/5/1/18), disclose that tetrabenazine is neuroprotective in Huntington's disease mice. However, Wang et al did not investigate the mortalities of treated and untreated mice and the test animals were all terminally anaesthetised at 13 months following the conclusion of the behavioural testing.

Tetrabenazine is an effective and safe drug for the treatment of a variety of hyperkinetic movement disorders and, in contrast to typical neuroleptics, has not been demonstrated to cause tardive dyskinesia. Nevertheless, tetrabenazine does exhibit a number of dose-related side effects including causing depression, parkinsonism, drowsiness, nervousness or anxiety, insomnia and, in rare cases, neuroleptic malignant syndrome, see for example the introductory section of WO2016/127133 (Neurocrine Biosciences).

The chemical structure of tetrabenazine is as shown below.

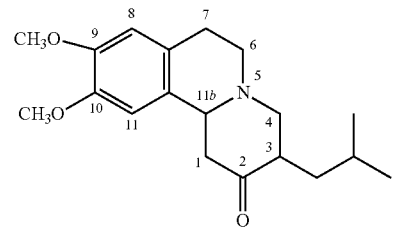

Structure of tetrabenazine

The compound has chiral centres at the 3 and 11b carbon atoms and hence can, theoretically, exist in a total of four isomeric forms, as shown below.

Possible tetrabenazine isomers

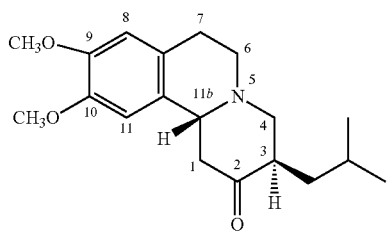

RR

SS

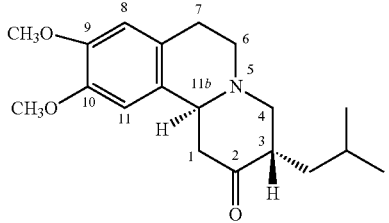

RS

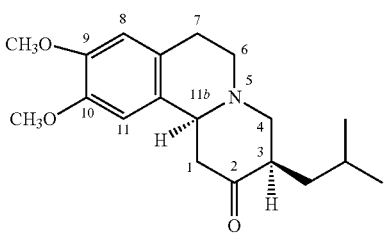

SR

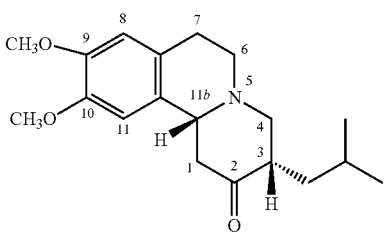

The stereochemistry of each isomer is defined using the "R and S" nomenclature developed by Cahn, Ingold and Prelog, see Advanced Organic Chemistry by Jerry March, 4th Edition, John Wiley & Sons, New York, 1992, pages 109-114. In this patent application, the designations "R" or "S" are given in the order of the position numbers of the carbon atoms. Thus, for example, RS is a shorthand notation for 3R, 11bS. Similarly, when three chiral centres are present, as in the dihydrotetrabenazines described below, the designations "R" or "S" are listed in the order of the carbon atoms 2, 3 and 11b. Thus, the 2R,3S, 11bS isomer is referred to in short hand form as RSS and so on.

Commercially available tetrabenazine is a racemic mixture of the RR and SS isomers and it would appear that the RR and SS isomers are the most thermodynamically stable isomers.

Tetrabenazine has somewhat poor and variable bioavailability. It is extensively metabolised by first-pass metabolism, and little or no unchanged tetrabenazine is typically detected in the urine. It is known that at least some of the metabolites of tetrabenazine are dihydrotetrabenazines formed by reduction of the 2-keto group in tetrabenazine.

Dihydrotetrabenazine (Chemical name: 2-hydroxy-3-(2-methylpropyl)-1,3,4,6,7,11b-hexahydro-9,10-dimethoxy-benzo(a)quinolizine) has three chiral centres and can therefore exist in any of the following eight optical isomeric forms:

Dihydrotetrabenazine isomers

RRR

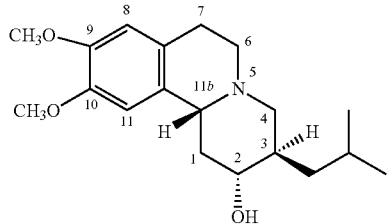

SSS

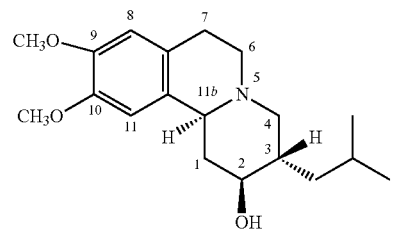

SRR

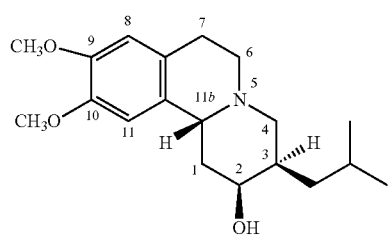

RSS

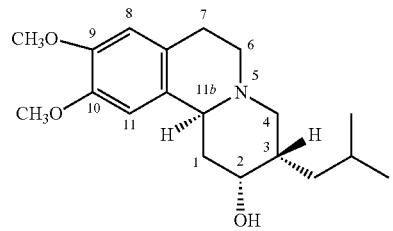

SSR

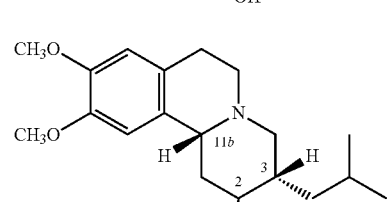

RRS

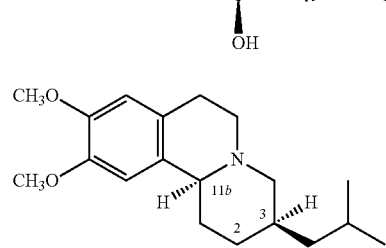

-continued

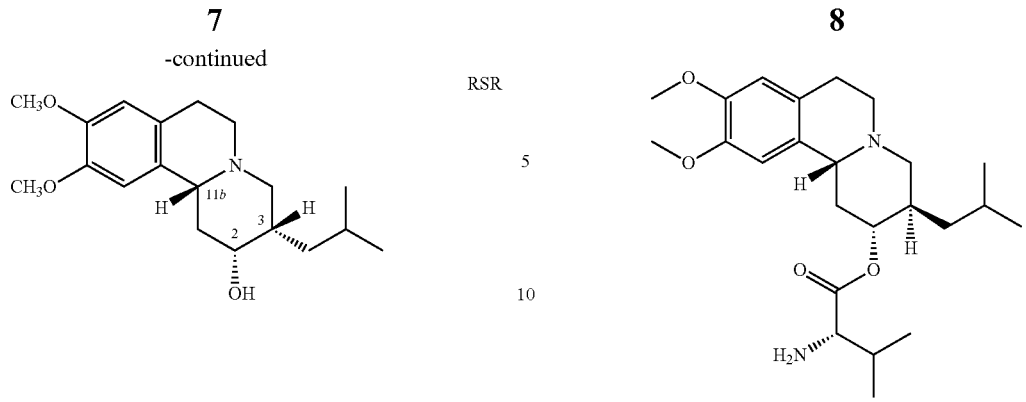

The synthesis and characterisation of all eight dihydrotetrabenazine isomers is described by Sun et al. (Eur. J. Med. Chem. (2011), 1841-1848).

Of the eight dihydrotetrabenazine isomers, four isomers are derived from the RR and SS isomers of the parent tetrabenazine, namely the RRR, SSS, SRR and RSS isomers.

The RRR and SSS isomers are commonly referred to as "alpha (α)" dihydrotetrabenazines and can be referred to individually as (+)-α-dihydrotetrabenazine and (−)-α-dihydrotetrabenazine respectively. The alpha isomers are characterised by a trans relative orientation of the hydroxyl and 2-methylpropyl substituents at the 2- and 3-positions —see for example, Kilbourn et al., Chirality, 9:59-62 (1997) and Brossi et al., Helv. Chim. Acta., vol. XLI, No. 193, pp1793-1806 (1958.

The SRR and RSS isomers are commonly referred to as "beta (β)" isomers and can be referred to individually as (+)-β-dihydrotetrabenazine and (−)-β-dihydrotetrabenazine respectively. The beta isomers are characterised by a cis relative orientation of the hydroxyl and 2-methylpropyl substituents at the 2- and 3-positions.

As discussed above, it is known that tetrabenazine exhibits a number of dose-related side effects including causing depression and parkinsonism (see WO2016/127133). It appears that these side-effects may also be caused by VMAT2 inhibition and that consequently it is difficult to separate the therapeutic effect of tetrabenazine and tetrabenazine-derived compounds from these side-effects (see Müller, "Valbenazine granted breakthrough drug status for treating tardive dyskinesia", Expert Opin. Investig. Drugs (2015), 24(6), pp. 737-742).

In an attempt to avoid or reduce the side-effects associated with tetrabenazine, a valine ester prodrug of (+)-α-dihydrotetrabenazine has been developed, known by its INN name, Valbenazine. The structure of Valbenazine is shown below:

In 2017, Valbenazine was approved for use in the treatment of tardive dyskinesia. Based on its use in treating tardive dyskinesia, it has been suggested that Valbenazine may also be useful in the treatment of other VMAT2-mediated diseases. However, to date, no clinical studies have been published relating to the use of Valbenazine in treating Huntington's Disease.

WO2007/007105 (Cambridge Laboratories (Ireland) Limited) describes studies on the SSR isomer of dihydrotetrabenazine (an isomer of dihydrotetrabenazine which is not produced in vivo through the metabolism of tetrabenazine) for halting or slowing the progress of one or more symptoms of Huntington's Disease. However, the experimental results in WO2007/007105 do not include any data on the mortalities of the test animals and hence no conclusions can be drawn from WO2007/007105 as to the effect of the compound on the lifespans of the animals.

WO2006/053067 (Prestwick Pharmaceuticals, Inc.) discloses the combination of amantadine and a tetrabenazine compound for treating hyperkinetic disorders, an example of which is given as Huntington's disease. Dihydrotetrabenazines are disclosed as examples of tetrabenazine compounds and, in one embodiment, the tetrabenazine compound is (+)-α-dihydrotetrabenazine. No biological data are presented in WO2006/053067: the experimental section merely sets out the protocols for studies intended to compare the absolute reduction in chorea in patients treated with amantadine alone, tetrabenazine alone and amantadine plus tetrabenazine and does not include any experimental results.

As far as the applicant is aware, there have been no studies to date which show the efficacy of (+)-α-dihydrotetrabenazine in treating Huntington's Disease or the management of symptoms associated with the disease (such as chorea).

The Invention

Whereas tetrabenazine is currently used to reduce the incidence and/or severity of the symptoms associated with Huntington's Disease (such as chorea), this does not treat the disease itself and hence tetrabenazine does not have a significant effect on a patient's prognosis.

However, it has now surprisingly been found that R6/2 mice treated with (+)-α-dihydrotetrabenazine had a prolonged lifespan compared to untreated control R6/2 mice and R6/2 mice that had been treated with tetrabenazine.

Based on these findings, it is envisaged that (+)-α-dihydrotetrabenazine and other (+)-dihydrotetrabenazine isomers will be useful, not only for managing the symptoms associated with Huntington's Disease, but also for reducing the life-shortening effect of the disease in mammals.

It is also envisaged that (+)-α-dihydrotetrabenazine and other (+)-dihydrotetrabenazine isomers will be useful in preventing or delaying the onset of late stage Huntington's Disease and/or life-threatening symptoms or events typically exhibited during late stage Huntington's disease.

Accordingly, in a first Embodiment, the invention provides a (+)-dihydrotetrabenazine isomer (e.g. (+)-α-dihydrotetrabenazine) or a pharmaceutically acceptable salt thereof for use in reducing the life-shortening effect of Huntington's Disease in mammals.

In another embodiment, the invention provides a (+)-dihydrotetrabenazine isomer (e.g. (+)-α-dihydrotetrabenazine) or a pharmaceutically acceptable salt thereof for use in preventing or delaying the onset of late stage Huntington's Disease. In another embodiment, the invention provides a (+)-dihydrotetrabenazine isomer (e.g. (+)-α-dihydrotetrabenazine) or a pharmaceutically acceptable salt thereof for use in preventing or delaying the onset of life-threatening symptoms or events exhibited during late stage Huntington's disease.

The term (+)-dihydrotetrabenazine isomer as used herein refers to those isomers having dextrorotatory (+) optical activity. Such activity can be measured by standard methods. The (+)-dihydrotetrabenazine isomers having dextrorotatory optical activity are believed to be those isomers having the R configuration at the 11b position of the molecule, namely the RRR, SRR, SSR and RSR isomers described above.

One subset of (+)-dihydrotetrabenazine isomers for use in each of the foregoing and following embodiments of the invention consists of the isomers wherein the hydrogen atoms at the 3- and 11b-positions are in the trans relative configuration, i.e. the RRR isomer ((+)-α-dihydrotetrabenazine) and the SRR isomer ((+)-β-dihydrotetrabenazine).

Another subset of (+)-dihydrotetrabenazine isomers for use in each of the foregoing and following embodiments of the invention consists of the isomers wherein the hydrogen atoms at the 3- and 11b-positions are in the cis relative configuration, i.e. the SSR and RSR isomer.

In one particular sub-embodiment within each of the foregoing and following embodiments, the (+)-dihydrotetrabenazine isomer is the RRR isomer ((+)-α-dihydrotetrabenazine).

In another particular sub-embodiment within each of the foregoing and following embodiments, the (+)-dihydrotetrabenazine isomer is the SRR isomer ((+)-β-dihydrotetrabenazine).

In another Embodiment, the invention provides a method of reducing the life-shortening effect of Huntington's Disease in a mammal, the method comprising administering an effective amount of a (+)-dihydrotetrabenazine isomer (e.g. (+)-α-dihydrotetrabenazine) or a pharmaceutically acceptable salt thereof to a mammalian subject in need thereof.

In another Embodiment, the invention provides the use of a (+)-dihydrotetrabenazine isomer (e.g. (+)-α-dihydrotetrabenazine) or a pharmaceutically acceptable salt thereof for the manufacture of a medicament for reducing the life-shortening effect of Huntington's Disease in mammals.

As discussed above, Huntington's Disease is caused by multiple CAG repeats in the IT 15 gene located on the short arm of chromosome 4p16.3. Accordingly, in further embodiments there are provided:

A (+)-dihydrotetrabenazine isomer (e.g. (+)-α-dihydrotetrabenazine) or a pharmaceutically acceptable salt thereof for use in reducing the life-shortening effect of a disease in mammals wherein the disease is characterised by a mutation in the IT15 gene of the mammal.

A method of reducing the life-shortening effect of a disease in a mammal wherein the disease is characterised by a mutation in the IT15 gene of the mammal, the method comprising administering an effective amount of a (+)-dihydrotetrabenazine isomer (e.g. (+)-α-dihydrotetrabenazine) or a pharmaceutically acceptable salt thereof to a mammalian subject in need thereof.

The use of a (+)-dihydrotetrabenazine isomer (e.g. (+)-α-dihydrotetrabenazine) or a pharmaceutically acceptable salt in the manufacture of a medicament for reducing the life-shortening effect of a disease in a mammal wherein the disease is characterised by a mutation in the IT 15 gene of the mammal.

The life shortening effect of the disease can be demonstrated by comparing the lifespan of a genetically modified test animal (e.g. a mouse model such as the R6/2 HD model discussed above) carrying a model of the disease with a wild-type animal. The life-shortening reducing effect of the a (+)-dihydrotetrabenazine isomer (e.g. (+)-α-dihydrotetrabenazine) or pharmaceutically acceptable salt thereof can be demonstrated by comparing the mean survival time of a group of mammals suffering from the disease or an appropriate model thereof, and treated with the (+)-dihydrotetrabenazine isomer (e.g. (+)-α-dihydrotetrabenazine) or pharmaceutically acceptable salt thereof, against the mean survival time of a control group of mammals who are suffering from the disease or the appropriate model thereof but who have not been treated with a (+)-dihydrotetrabenazine isomer (e.g. (+)-α-dihydrotetrabenazine) or a pharmaceutically acceptable salt thereof.

In further Embodiments, there are also provided:

A (+)-dihydrotetrabenazine isomer (e.g. (+)-α-dihydrotetrabenazine) for use, a method or a use as described above wherein the mutation results in 36 or more CAG repeats in the IT15 gene.

A (+)-dihydrotetrabenazine isomer (e.g. (+)-α-dihydrotetrabenazine) for use, a method or a use as described above wherein the mutation results in 38 or more CAG repeats in the IT15 gene.

A (+)-dihydrotetrabenazine isomer (e.g. (+)-α-dihydrotetrabenazine) for use, a method or a use as described above wherein the mutation results in 40 or more CAG repeats in the IT15 gene.

A (+)-dihydrotetrabenazine isomer (e.g. (+)-α-dihydrotetrabenazine) for use, a method or a use as described above wherein the mutation results in 42 or more CAG repeats in the IT15 gene.

A (+)-dihydrotetrabenazine isomer (e.g. (+)-α-dihydrotetrabenazine) for use, a method or a use as described above wherein the mutation results in 44 or more CAG repeats in the IT15 gene.

A (+)-dihydrotetrabenazine isomer (e.g. (+)-α-dihydrotetrabenazine) for use, a method or a use as described above wherein the mutation results in 46 or more CAG repeats in the IT15 gene.

A (+)-dihydrotetrabenazine isomer (e.g. (+)-α-dihydrotetrabenazine) for use, a method or a use as described above wherein the mutation results in 48 or more CAG repeats in the IT15 gene.

A (+)-dihydrotetrabenazine isomer (e.g. (+)-α-dihydrotetrabenazine) for use, a method or a use as described above wherein the mutation results in 50 or more CAG repeats in the IT15 gene.

A (+)-dihydrotetrabenazine isomer (e.g. (+)-α-dihydrotetrabenazine) for use, a method or a use as described above wherein the mutation results in 52 or more CAG repeats in the IT15 gene.

A (+)-dihydrotetrabenazine isomer (e.g. (+)-α-dihydrotetrabenazine) for use, a method or a use as described above wherein the mutation results in 54 or more CAG repeats in the IT15 gene.

The IT15 gene encodes the Huntingtin protein and therefore mutations (and in particular excessive CAG repeats) in the IT15 gene result in a mutated form of the Huntingtin protein. Accordingly, in further embodiments there are provided:

A (+)-dihydrotetrabenazine isomer (e.g. (+)-α-dihydrotetrabenazine) or a pharmaceutically acceptable salt thereof for use in reducing the life-shortening effect of a disease in mammals wherein the disease is characterised by the presence of a mutated form of the Huntingtin protein.

A method of reducing the life-shortening effect of a disease in a mammal wherein the disease is characterised by the presence of a mutated form of the Huntingtin protein, the method comprising administering an effective amount of a (+)-dihydrotetrabenazine isomer (e.g. (+)-α-dihydrotetrabenazine) or a pharmaceutically acceptable salt thereof to a mammalian subject in need thereof.

The use of a (+)-dihydrotetrabenazine isomer (e.g. (+)-α-dihydrotetrabenazine) or a pharmaceutically acceptable salt in the manufacture of a medicament for reducing the life-shortening effect of a disease in a mammal wherein the disease is characterised by the presence of a mutated form of the Huntingtin protein.

A (+)-dihydrotetrabenazine isomer (e.g. (+)-α-dihydrotetrabenazine) or a pharmaceutically acceptable salt thereof for use in reducing the life-shortening effect of a disease in mammals wherein the disease is caused by the presence of a mutated form of the Huntingtin protein.

A method of reducing the life-shortening effect of a disease in a mammal wherein the disease is caused by the presence of a mutated form of the Huntingtin protein, the method comprising administering an effective amount of a (+)-dihydrotetrabenazine isomer (e.g. (+)-α-dihydrotetrabenazine) or a pharmaceutically acceptable salt thereof to a mammalian subject in need thereof.

The use of a (+)-dihydrotetrabenazine isomer (e.g. (+)-α-dihydrotetrabenazine) or a pharmaceutically acceptable salt in the manufacture of a medicament for reducing the life-shortening effect of a disease in a mammal wherein the disease is caused by the presence of a mutated form of the Huntingtin protein.

In the above Embodiments, the mutated form of the Huntingtin protein may result from the number of CAG repeats in the IT15 gene which encodes the Huntingtin protein (as defined above). For example, the mutated form of the Huntingtin protein may result from the presence of 38 or greater, 40 or greater, 42 or greater, 44 or greater, 46 or greater, 48 or greater, 50 or greater, 52 or greater or 54 or greater CAG repeats on the IT-15 gene.

In further embodiments there are provided:

(+)-α-Dihydrotetrabenazine or a pharmaceutically acceptable salt thereof for use in slowing or halting the progress of Huntington's Disease in a patient.

A method of slowing or halting the progress of Huntington's Disease in a patient, the method comprising administering an effective amount of (+)-α-dihydrotetrabenazine or a pharmaceutically acceptable salt thereof to the patient.

The use of (+)-α-dihydrotetrabenazine or a pharmaceutically acceptable salt thereof in the manufacture of a medicament for slowing or halting the progress of Huntington's Disease in a patient.

In further embodiments there are provided:

(+)-α-Dihydrotetrabenazine) or a pharmaceutically acceptable salt thereof for use in reducing the incidence or severity of one or more symptoms associated with Huntington's Disease in a patient.

A method of reducing the incidence or severity of one or more symptoms associated with Huntington's Disease in a patient, the method comprising administering an effective amount of (+)-α-dihydrotetrabenazine or a pharmaceutically acceptable salt thereof to the patient.

The use of (+)-α-dihydrotetrabenazine or a pharmaceutically acceptable salt in the manufacture of a medicament for reducing the incidence or severity of one or more symptoms associated with Huntington's Disease.

(+)-α-Dihydrotetrabenazine) or a pharmaceutically acceptable salt thereof for use in halting or slowing the progress of one or more symptoms associated with Huntington's Disease in a patient.

A method of halting or slowing the progress of one or more symptoms associated with Huntington's Disease in a patient, the method comprising administering an effective amount of (+)-α-dihydrotetrabenazine) or a pharmaceutically acceptable salt thereof to the patient.

The use of (+)-α-dihydrotetrabenazine) or a pharmaceutically acceptable salt in the manufacture of a medicament for halting or slowing the progress of one or more symptoms associated with Huntington's Disease in a patient.

The one or more symptoms may be selected from involuntary chorea, tremors, twitches and degeneration in gait.

Alternatively or additionally, the symptoms may be life-threatening symptoms or events such as the life threatening symptoms or events typically encountered in late stage Huntington's disease.

Life threatening symptoms or events encountered in late stage Huntington's disease typically arise out of a loss of muscular control and hence a subject's inability to control their movements, and/or a loss of spontaneous movement. An inability to control movement can lead to pneumonia arising from an inability to clear the lungs and an increased risk of aspirating food or drink. An inability to control movement can also result in severe difficulties in swallowing which in turn will result in an inability to eat or drink, thereby leading potentially to malnutrition.

Sufferers from Huntington's Disease also have a higher incidence of choking and gastrointestinal diseases (such as cancer of the pancreas).

Other life threatening symptoms or events often encountered in late stage Huntington's disease include symptoms or events associated with cardiac disease.

The ability to prevent or delay the onset of these symptoms or events can therefore increase the life expectancy of a patient with the disease.

A particular group of life-threatening symptoms or events, the onset of which it is envisaged will be prevented or delayed in accordance with the invention, consists of:

pneumonia arising from an inability to clear the lungs; and/or malnutrition and/or acute dehydration arising from an inability to swallow; and/or choking; and/or life threatening symptoms of cardiac disease.

In a particular embodiment, the life-threatening symptoms, the onset of which it is envisaged will be prevented or delayed in accordance with the invention, are symptoms that arise from an inability to move or exhibit muscular control, an inability to coordinate movements or an inability to carry out spontaneous movements. Examples of such symptoms or events include pneumonia, choking and malnutrition as discussed above.

Accordingly, in further embodiments the invention provides:

A (+)-dihydrotetrabenazine isomer (e.g. (+)-α-dihydrotetrabenazine) or a pharmaceutically acceptable salt thereof for use in preventing or delaying the onset of one or more life-threatening symptoms or events associated with Huntington's Disease in a subject.

A method of preventing or delaying the onset of one or more life-threatening symptoms or events associated with Huntington's Disease in a subject, the method comprising administering an effective amount of a (+)-dihydrotetrabenazine isomer (e.g. (+)-α-dihydrotetrabenazine) or a pharmaceutically acceptable salt thereof to the subject.

The use of a (+)-dihydrotetrabenazine isomer (e.g. (+)-α-dihydrotetrabenazine) or a pharmaceutically acceptable salt in the manufacture of a medicament for preventing or delaying the onset of one or more life-threatening symptoms or events associated with Huntington's Disease in a subject.

A (+)-dihydrotetrabenazine isomer (e.g. (+)-α-dihydrotetrabenazine) or a pharmaceutically acceptable salt thereof for use in increasing the life expectancy in a subject suffering from Huntington's Disease.

A method of increasing the life expectancy in a subject suffering from Huntington's Disease, the method comprising administering an effective amount of a (+)-dihydrotetrabenazine isomer (e.g. (+)-α-dihydrotetrabenazine) or a pharmaceutically acceptable salt thereof to the subject.

The use of a (+)-dihydrotetrabenazine isomer (e.g. (+)-α-dihydrotetrabenazine) or a pharmaceutically acceptable salt in the manufacture of a medicament for increasing the life expectancy in a subject suffering from Huntington's Disease.

Experimental results presented in Example 1 below demonstrate the effectiveness of a (+)-dihydrotetrabenazine isomer (e.g. (+)-α-dihydrotetrabenazine) in reducing tremors associated with Huntington's Disease. Accordingly, in particular embodiments of the invention, the symptoms associated with Huntington's Disease in the patient which are halted or slowed are (or comprise) tremors.

In further Embodiments, there are also provided:

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 0.5 mg to 500 mg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 0.5 mg to 400 mg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 0.5 mg to 300 mg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 0.5 mg to 250 mg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 10 mg to 500 mg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 20 mg to 500 mg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 50 mg to 500 mg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 20 mg to 400 mg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 50 mg to 400 mg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 50 mg to 300 mg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 0.5 mg/kg to 5 mg/kg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 1 mg/kg to 5 mg/kg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 1 mg/kg to 4 mg/kg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 1.5 mg/kg to 3.5 mg/kg.

A (+)-dihydrotetrabenazine isomer (e.g. (+)-α-dihydrotetrabenazine) for use, a method or a use as described herein comprising administering to the mammal a (+)-dihydrotetrabenazine isomer (e.g. (+)-α-dihydrotetrabenazine) in an amount of from 1.5 mg/kg to 3 mg/kg.

The amounts given above are typically daily amounts of the (+)-dihydrotetrabenazine isomer to be administered.

In the embodiments described herein subjects treated in accordance with the invention are typically mammals. The mammals may be non-human mammals such as mice and rats, or they may, for example, be humans.

(+)-α-Dihydrotetrabenazine is believed to have the chemical structure shown in Formula (I) below.

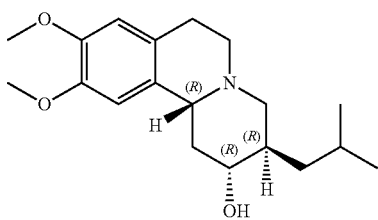

Accordingly, in another Embodiment, the invention provides an Invention as defined herein wherein the (+)-α-dihydrotetrabenazine has a chemical formula as shown in Formula (I).

(+)-β-Dihydrotetrabenazine is believed to have the chemical structure shown in Formula (II) below.

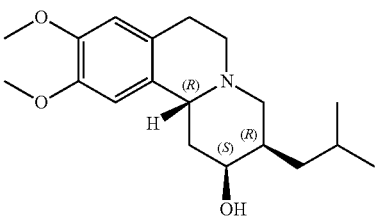

Accordingly, in another Embodiment, the invention provides an Invention as defined herein wherein the (+)-β-dihydrotetrabenazine has a chemical formula as shown in Formula (II).

In each of the above Embodiments, the (+)-dihydrotetrabenazine isomer (e.g. (+)-α-dihydrotetrabenazine) or pharmaceutically acceptable salt thereof typically has an isomeric purity of greater than 60%.

The term "isomeric purity" in the present context, i.e. when used in relation to a given (+)-dihydrotetrabenazine isomer (e.g. (+)-α-dihydrotetrabenazine), refers to the amount of that (+)-α-dihydrotetrabenazine isomer (e.g. (+)-α-dihydrotetrabenazine ((+)-α-DHTBZ)) present relative to the total amount or concentration of dihydrotetrabenazine of all isomeric forms. For example, if 90% of the total dihydrotetrabenazine present in the composition is (+)-α-DHTBZ dihydrotetrabenazine, then the isomeric purity is 90%.

Accordingly, in further Embodiments of the Invention, there is provided:
An Invention as defined herein wherein the (+)-dihydrotetrabenazine isomer (e.g. (+)-α-DHTBZ or (+)-β-DHTBZ)) has an isomeric purity of greater than 60%.
An Invention as defined herein wherein the (+)-dihydrotetrabenazine isomer (e.g. (+)-α-DHTBZ or (+)-β-DHTBZ) has an isomeric purity of greater than 65%.
An Invention as defined herein wherein the (+)-dihydrotetrabenazine isomer (e.g. (+)-α-DHTBZ or (+)-β-DHTBZ) has an isomeric purity of greater than 70%.
An Invention as defined herein wherein the (+)-dihydrotetrabenazine isomer (e.g. (+)-α-DHTBZ or (+)-β-DHTBZ) has an isomeric purity of greater than 75%.
An Invention as defined herein the (+)-dihydrotetrabenazine isomer (e.g. (+)-α-DHTBZ or (+)-β-DHTBZ) has an isomeric purity of greater than 80%.
An Invention as defined herein wherein the (+)-dihydrotetrabenazine isomer (e.g. (+)-α-DHTBZ or (+)-β-DHTBZ) has an isomeric purity of greater than 85%.
An Invention as defined herein wherein the (+)-dihydrotetrabenazine isomer (e.g. (+)-α-DHTBZ or (+)-β-DHTBZ) has an isomeric purity of greater than 90%.
An Invention as defined herein wherein the (+)-dihydrotetrabenazine isomer (e.g. (+)-α-DHTBZ or (+)-β-DHTBZ) has an isomeric purity of greater than 91%.
An Invention as defined herein wherein the (+)-dihydrotetrabenazine isomer (e.g. (+)-α-DHTBZ or (+)-β-DHTBZ) has an isomeric purity of greater than 92%.
An Invention as defined herein wherein the (+)-dihydrotetrabenazine isomer (e.g. (+)-α-DHTBZ or (+)-β-DHTBZ) has an isomeric purity of greater than 93%.
An Invention as defined herein wherein the (+)-dihydrotetrabenazine isomer (e.g. (+)-α-DHTBZ or (+)-β-DHTBZ) has an isomeric purity of greater than 94%.
An Invention as defined herein wherein the (+)-dihydrotetrabenazine isomer (e.g. (+)-α-DHTBZ or (+)-β-DHTBZ) has an isomeric purity of greater than 95%.
An Invention as defined herein wherein the (+)-dihydrotetrabenazine isomer (e.g. (+)-α-DHTBZ or (+)-β-DHTBZ) has an isomeric purity of greater than 96%.
An Invention as defined herein wherein the (+)-dihydrotetrabenazine isomer (e.g. (+)-α-DHTBZ or (+)-β-DHTBZ) has an isomeric purity of greater than 97%.
An Invention as defined herein wherein the (+)-dihydrotetrabenazine isomer (e.g. (+)-α-DHTBZ or (+)-β-DHTBZ) has an isomeric purity of greater than 98%.
An Invention as defined herein wherein the (+)-dihydrotetrabenazine isomer (e.g. (+)-α-DHTBZ or (+)-β-DHTBZ) has an isomeric purity of greater than 99%.
An Invention as defined herein wherein the (+)-dihydrotetrabenazine isomer (e.g. (+)-α-DHTBZ or (+)-β-DHTBZ) has an isomeric purity of greater than 99.5%.
An Invention as defined herein wherein the (+)-dihydrotetrabenazine isomer (e.g. (+)-α-DHTBZ or (+)-β-DHTBZ) has an isomeric purity of greater than 99.9%.

Prior to administration of a (+)-dihydrotetrabenazine isomer (e.g. (+)-α-dihydrotetrabenazine or (+)-β-dihydrotetrabenazine), a patient may be screened to determine whether the patient is suffering from a disease of condition which is characterised by the presence of multiple CAG repeats in the Huntingtin gene.

Such screening tests may make use of the polymerase chain reaction (PCR) to detect the number of CAG repeats on the IT-15 gene and are widely available to allow a prediction to be made whether or not a patient will develop the symptoms of e.g. Huntington's disease (see for example the review by M. Hayden et al, Am. J. Hum. Genet. 55:606-617 (1994); the article by S. Hersch, "The Neurogenetics Genie: Testing for the Huntington's disease mutation." Neurol. 1994; 44:1369-1373; and the article by R. R. Brinkman et al. (1997) "The likelihood of being affected with Huntington disease by a particular age, for a specific CAG size", Am. J. Hum. Genet. 60:1202-1210.)

Accordingly, in further embodiments, the invention provides:
A (+)-dihydrotetrabenazine isomer (e.g. (+)-α-dihydrotetrabenazine or (+)-β-dihydrotetrabenazine) or a pharmaceutically acceptable salt thereof for use in the reducing the life-shortening effect of a disease in a patient who has been screened and has been determined as suffering from, or being at risk of suffering from, the disease, wherein the disease is characterised by the presence of 36 or greater CAG repeats on the IT-15 gene.

The use of a (+)-dihydrotetrabenazine isomer (e.g. (+)-α-dihydrotetrabenazine or (+)-β-dihydrotetrabenazine) or a pharmaceutically acceptable salt thereof in the manufacture of a medicament for reducing the life-shortening effect of a disease in a patient who has been screened and has been determined as suffering from, or being at risk of suffering from, the disease, wherein the disease is characterised by the presence of 36 or greater CAG repeats on the IT-15 gene.

A method for the diagnosis and reducing the life-shortening effect of a disease wherein the disease is characterised by the presence of 36 or greater CAG repeats on the IT-15 gene, which method comprises (i) screening a patient to determine whether the disease from which the patient is or may be suffering is one which is characterised by the presence of 36 or greater CAG repeats on the IT-15 gene; and (ii) where it is indicated that the disease is characterised as such, thereafter administering to the patient an effective amount of a (+)-dihydrotetrabenazine isomer (e.g. (+)-α-dihydrotetrabenazine or (+)-β-dihydrotetrabenazine) of a pharmaceutically acceptable salt thereof.

The disease may be characterised by the presence of 38 or greater, 40 or greater, 42 or greater, 44 or greater, 46 or greater, 48 or greater, 50 or greater, 52 or greater or 54 of greater CAG repeats on the IT-15 gene. In one embodiment, the disease is Huntington's Disease.

A reduction in life expectancy has also been reported in schizophrenic patients suffering from tardive dyskinesia (see the article entitled "The life expectancy of schizophrenic patients with tardive dyskinesia" by H. Inada et al., Human Psychopharmacology: Clinical & Experimental, July/August 1992). In addition to treating Huntington's disease as disclosed herein, dihydrotetrabenazine isomers can also be used to treat other movement disorders such as tardive dyskinesia (see our International patent applications numbers PCT/EP2018/058069, PCT/EP2018/05109 and PCT/EP2018/058088, the contents of which are incorporated herein in their entirety). It is envisaged that the ability of a (+)-dihydrotetrabenazine isomer to bring about a reduction in the life-shortening effect of a movement disorder disease (as exemplified herein in relation to Huntington's Disease) may be applicable also to other movement disorder diseases and in particular to schizophrenic patients suffering from tardive dyskinesia.

Accordingly, in a further Embodiment, the invention provides a (+)-dihydrotetrabenazine isomer (e.g. (+)-α-dihydrotetrabenazine or (+)-β-dihydrotetrabenazine) or a pharmaceutically acceptable salt thereof for use in reducing the life-shortening effect of tardive dyskinesia in a schizophrenic patient.

In another Embodiment, the invention provides a method of reducing the life-shortening effect of tardive dyskinesia in a schizophrenic patient, the method comprising administering an effective amount of a (+)-dihydrotetrabenazine isomer (e.g. (+)-α-dihydrotetrabenazine) or a pharmaceutically acceptable salt thereof to a patient in need thereof.

In another Embodiment, the invention provides the use of a (+)-dihydrotetrabenazine isomer (e.g. (+)-α-dihydrotetrabenazine or (+)-β-dihydrotetrabenazine) or a pharmaceutically acceptable salt thereof for the manufacture of a medicament for reducing the life-shortening effect of tardive dyskinesia in a schizophrenic patient.

The amounts of (+)-dihydrotetrabenazine isomer (e.g. (+)-α-dihydrotetrabenazine) or a pharmaceutically acceptable salt thereof used in the foregoing three embodiments can be as described below or as described above in relation to the treatment of Huntington's Disease.

In each of the foregoing aspects and embodiments of the invention, the (+)-dihydrotetrabenazine isomer (e.g. (+)-α-dihydrotetrabenazine) or a pharmaceutically acceptable salt thereof is typically not used in combination with amantadine or its salts. Thus, the (+)-dihydrotetrabenazine isomer (e.g. (+)-α-dihydrotetrabenazine) or a pharmaceutically acceptable salt thereof is typically not administered either simultaneously or sequentially together with amantadine or its salts to patients suffering from Huntington's disease, or carrying any of the markers for Huntington's disease as described above, or for any other therapeutic purpose.

Pharmaceutically Acceptable Salts

Unless the context requires otherwise, a reference in this application to a (+)-dihydrotetrabenazine isomer (e.g. (+)-α-dihydrotetrabenazine or (+)-β-dihydrotetrabenazine), includes within its scope not only the free base of the (+)-dihydrotetrabenazine isomer (e.g. (+)-α-dihydrotetrabenazine) but also its salts, and in particular acid addition salts.

Accordingly, in further Embodiments of the Invention, there is provided:

An Invention as defined herein wherein the (+)-dihydrotetrabenazine isomer (e.g. (+)-α-dihydrotetrabenazine) is in the form of a free base.

An Invention as defined herein wherein the (+)-dihydrotetrabenazine isomer (e.g. (+)-α-dihydrotetrabenazine) is in the form of a pharmaceutically acceptable salt.

An Invention as defined herein wherein the pharmaceutically acceptable salt is an acid addition salt.

Acid addition salts may be formed with a variety of acids, both inorganic and organic. The salt forms of the compounds of the invention are pharmaceutically acceptable salts, and examples of pharmaceutically acceptable salts are discussed in Berge et al., 1977, "Pharmaceutically Acceptable Salts," J. Pharm. Sci., Vol. 66, pp. 1-19.

Particular acids from which the acid addition salts are formed include acids having a pKa value of less than 3.5 and more usually less than 3. For example, the acid addition salts can be formed from an acid having a pKa in the range from +3.5 to −3.5.

Acid addition salts can be prepared by the methods described herein or conventional chemical methods such as the methods described in Pharmaceutical Salts: Properties, Selection, and Use, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the appropriate base or acid in water or in an organic solvent, or in a mixture of the two; generally, nonaqueous media such as ether, ethyl acetate, ethanol, isopropanol, or acetonitrile are used.

Particular examples of acid addition salts include salts formed with an acid selected from the group consisting of hydrochloric acid, sulphuric acid, benzenesulphonic acid and succinic acid. Such salts can be formed by the methods described in our International patent application WO2018/178251, the contents of which are incorporated herein by reference.

In one embodiment, the (+)-α-dihydrotetrabenazine is administered to the patient as the succinate salt due to its enhanced a higher solubility and greater thermal stability, with a reduced tendency to form polymorphs, compared to the free base and other salts of (+)-α-dihydrotetrabenazine.

Isotopes

The (+)-dihydrotetrabenazine isomer (e.g. (+)-α-dihydrotetrabenazine) may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{11}C$, $^{12}C$, $^{13}C$ and $^{14}C$ and $^{16}O$ and $^{18}O$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention, the (+)-dihydrotetrabenazine isomer (e.g. (+)-α-dihydrotetrabenazine) contains no radioactive isotopes. Such compounds are preferred for therapeutic use. In another embodiment, however, the (+)-dihydrotetrabenazine isomer (e.g. (+)-α-dihydrotetrabenazine) may contain one or more radioisotopes. Compounds containing such radioisotopes may be useful in a diagnostic context. In one subset of each of the foregoing embodiments of the invention, the (+)-dihydrotetrabenazine isomer (e.g. (+)-α-dihydrotetrabenazine) may be other than one in which one or both of the methoxy groups present are replaced by trideuteromethoxy groups.

Solvates

The (+)-dihydrotetrabenazine isomer (e.g. (+)-α-dihydrotetrabenazine) may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates.

Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, IN, USA, 1999, ISBN 0-967-06710-3.

Alternatively, rather than existing as a hydrate, the compound of the invention may be anhydrous. Therefore, in another embodiment, the (+)-dihydrotetrabenazine isomer (e.g. (+)-α-dihydrotetrabenazine) is in an anhydrous form.

Methods for Preparation of (+)-α-dihydrotetrabenazine and (+)-β-dihydrotetrabenazine (+)-α-Dihydrotetrabenazine and the other (+)-dihydrotetrabenazine isomers can be prepared according to Yao et al., "Preparation and evaluation of tetrabenazine enantiomers and all eight stereoisomers of dihydrotetrabenazine as VMAT2 inhibitors", Eur. J. Med. Chem., (2011), 46, pp. 1841-1848.

(+)-α-Dihydrotetrabenazine (compound of formula (I)) can also be prepared from tetrabenazine according to the synthetic route shown in Scheme 1.

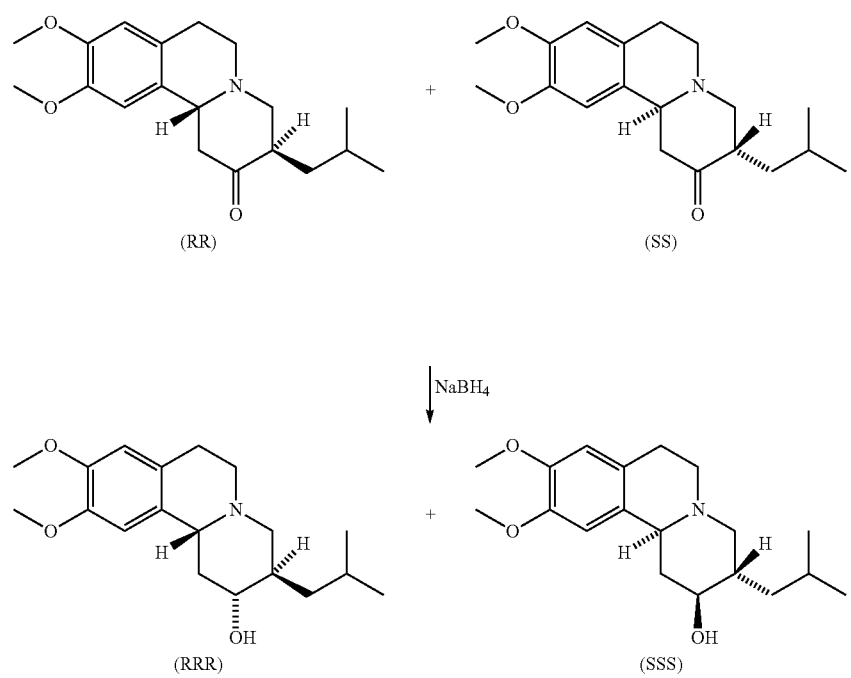

Scheme 1

-continued

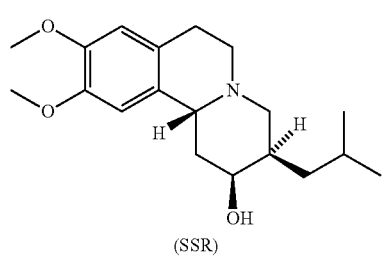
(SSR)

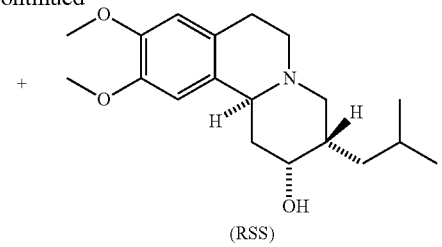
(RSS)

↓ Resolution of isomers (I)

Racemic tetrabenazine (3-isobutyl-9,10-dimethoxy-1,3,4,6,7,11b-hexahydro-2H-pyrido[2,1,a]isoquinolin-2-one) containing the RR and SS isomers of tetrabenazine is reduced with sodium borohydride to afford a mixture of four dihydrotetrabenazine isomers of which a racemic mixture of the α-dihydrotetrabenazines (RRR and SSS isomers) constitutes the major product and a racemic mixture of the β-dihydrotetrabenazines (the SRR and RSS isomers) constitutes a minor product. The β-dihydrotetrabenazines can be removed and isolated during an initial purification procedure, for example by chromatography or recrystallization and then the racemic α-dihydrotetrabenazines resolved (e.g. by recrystallisation with di-p-toluoyl-L-tartaric acid or (R)-(−)-camphorsulphonic acid or by chiral chromatography), to afford (+)-α-dihydrotetrabenazine (I) ((2R, 3R, 11bR)-3-isobutul-9,10-dimethox-1,3,4,6,7,11b-hexahydro-2H-pyrido[2,1,a]isoquinolin-2-ol). The stereochemical configuration of (+)-α-dihydrotetrabenazine can be determined, so example by forming a salt such as the succinate salt in crystalline form and the structure identified by X-ray crystallography.

(+)-β-Dihydrotetrabenazine (compound of formula (II)) can be prepared from tetrabenazine according to the synthetic route shown in Scheme 2.

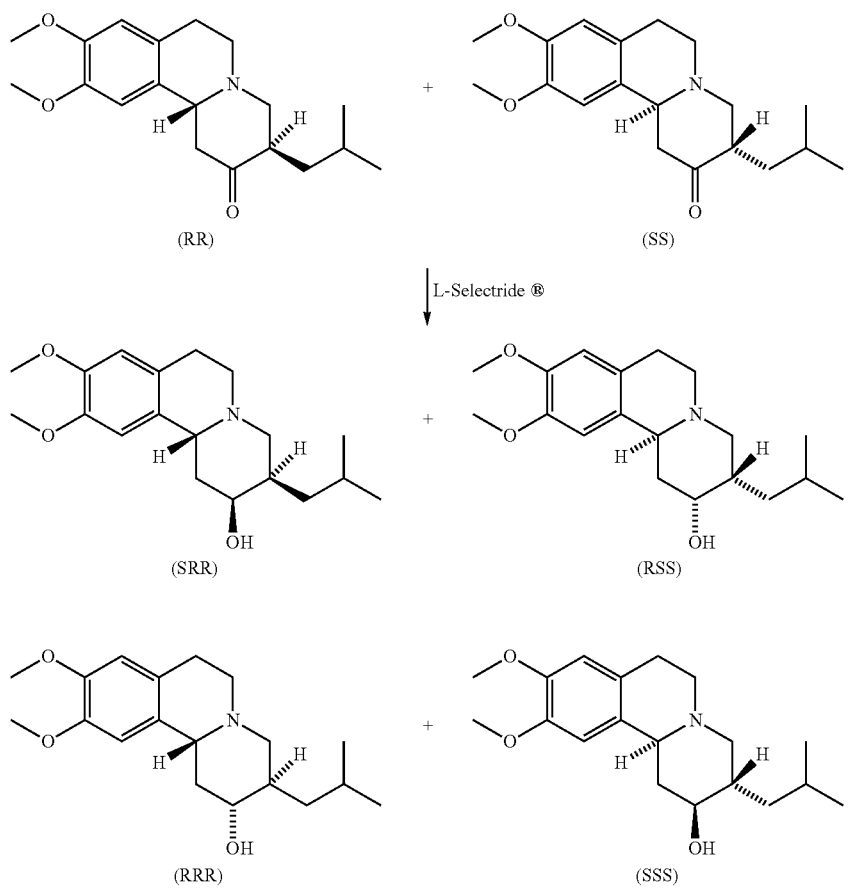

Scheme 2

Racemic tetrabenazine (3-isobutyl-9,10-dimethyoxy-1,3,4,6,7,11b-hexahydro-2H-pyrido[2,1, a]isoquinolin-2-one) containing the RR and SS isomers of tetrabenazine is reduced with sodium borohydride to afford a mixture of four dihydrotetrabenazine isomers of which a racemic mixture of the β-dihydrotetrabenazines (SRR and RSS isomers) constitutes the major product and a racemic mixture of the α-dihydrotetrabenazines (the RRR and SSS isomers) constitutes a minor product. The α-dihydrotetrabenazines can be removed during an initial purification procedure, for example by chromatography or recrystallization and then the racemic β-dihydrotetrabenazines resolved (e.g. by recrystallisation with di-p-toluoyl-L-tartaric acid or (R)-(−)-camphorsulfonic acid or by chiral chromatography), to afford (+)-β-dihydrotetrabenazine (III) ((2S, 3R, 11bR)-3-isobutyl-9,10-dimethoxy-1,3,4,6,7,11b-hexahydro-2H-pyrido[2,1, a]isoquinolin-2-ol). The stereochemical configuration of (+)-β-dihydrotetrabenazine can be determined, so example by forming a salt such as the mesylate salt in crystalline form and the structure identified by X-ray crystallography.

Pharmaceutical Formulations and Methods of Treatment

The (+)-dihydrotetrabenazine isomer (e.g. (+)-α-dihydrotetrabenazine or (+)-β-dihydrotetrabenazine) may be administered to patients as the pure compound but, more usually, they will be administered in the form of pharmaceutical compositions.

The pharmaceutical compositions of the Invention can be in any form suitable for oral, parenteral, topical, intranasal, intrabronchial, ophthalmic, otic, rectal, intra-vaginal, or transdermal administration. Where the formulations are intended for oral administration, they can be formulated for delivery to the gastrointestinal tract or for transmucosal delivery (for example by sublingual or buccal administration). Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules, caplets, pills, lozenges, syrups, solutions, sprays, powders, granules, elixirs and suspensions, sublingual tablets, sprays, wafers or patches and buccal patches.

Pharmaceutical compositions containing the dihydrotetrabenazine compound of the invention can be formulated in accordance with known techniques, see for example, Remington's Pharmaceutical Sciences, Mack Publishing Company, Easton, PA, USA.

Thus, tablet compositions can contain a unit dosage of active compound together with an inert diluent or carrier such as a sugar or sugar alcohol, e.g.; lactose, sucrose, sorbitol or mannitol; and/or a non-sugar derived diluent such as sodium carbonate, calcium phosphate, talc, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g. tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped mouldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

Particular pharmaceutical compositions of the invention are compositions selected from:
  Sublingual compositions;
  Intranasal;
  Pellets or tablets formulated to provide release kinetics corresponding to zero order release of the active compound;

Pellets or tablets formulated to provide first fast release followed by constant rate release (zero order) of the active compound;

Pellets or tablets formulated to provide a mixture of first order and zero order release of the active compound; and Pellets or tablets formulated to provide a combination of zero order and first order release of the active compound; and optionally a further order of release of the active compound selected from second, third and fourth orders of release and combinations thereof.

Pellets and tablets formulated to provide release kinetics of the types defined above can be prepared according to methods well known the skilled person; for example as described in Remington's Pharmaceutical Sciences (idem) and "Remington—The Science and Practice of Pharmacy, 21st edition, 2006, ISBN 0-7817-4673-6.

The compound of the invention will generally be presented in unit dosage form and, as such, will typically contain sufficient compound to provide a desired level of biological activity. For example, a formulation intended for oral administration may contain from 2 milligrams to 200 milligrams of active ingredient, more usually from 10 milligrams to 100 milligrams, for example, 12.5 milligrams, 25 milligrams and 50 milligrams.

The active compound will be administered to a patient in need thereof (for example a human or animal (e.g. mammal) patient) in an amount sufficient to achieve the desired therapeutic effect.

The compound will generally be administered to a subject in need of such administration, for example a human or animal (e.g. mammal) patient, preferably a human.

The compound of the invention will typically be administered in amounts that are therapeutically or prophylactically useful and which generally are non-toxic.

However, in certain situations, the benefits of administering a dihydrotetrabenazine compound of the invention may outweigh the disadvantages of any toxic effects or side effects, in which case it may be considered desirable to administer compounds in amounts that are associated with a degree of toxicity.

A typical daily dose of the compound of the invention can be in the range from 0.025 milligrams to 5 milligrams per kilogram of body weight, for example up to 3 milligrams per kilogram of bodyweight, and more typically 0.15 milligrams to 5 milligrams per kilogram of bodyweight although higher or lower doses may be administered where required.

By way of example, an initial starting dose of 5 mg to 15 mg (e.g. 10 mg or 12.5 mg) may be administered 2 to 3 times a day. The dosage can be increased by an amount in the range 5 mg to 15 mg (e.g. 10 mg or 12.5 mg) a day every 3 to 5 days until the maximal tolerated and effective dose is reached for the individual as determined by the physician. Ultimately, the quantity of compound administered will be commensurate with the nature of the disease or physiological condition being treated and the therapeutic benefits and the presence or absence of side effects produced by a given dosage regimen, and will be at the discretion of the physician.

EXAMPLES

Figure 1:
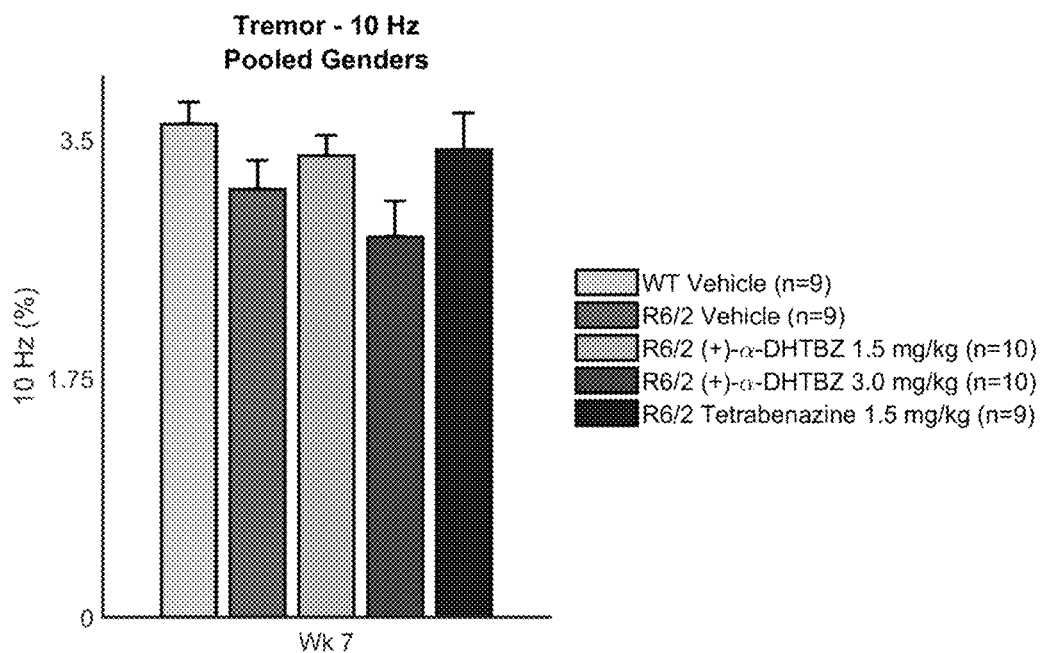
FIG. 1 shows the tremor power spectral density at 10 Hz of WT mice treated with vehicle and R6/2 mice treated with vehicle, (+)-α-DHTBZ 1.5 mg/kg, (+)-α-DHTBZ 3.0 mg/kg and TBZ 1.5 mg/kg.

The following non-limiting example illustrates the biological properties of (+)-α-dihydrotetrabenazine.

Example 1

Effect of (+)-α-Dihydrotetrabenazine in a R6/2 Mouse Model

The objective of this study was to investigate the efficacy of (+)-α-dihydrotetrabenazine in the R6/2 mouse model of Huntington's disease. The mice were treated with (+)-α-dihydrotetrabenazine ((+)-α-DHTBZ), tetrabenazine (TBZ) or vehicle starting at 4 weeks of age and continuing until 13 weeks of age.

In total, 38 male R6/2 mice and 9 wild type (WT) littermates were used in the study. Mice were dosed from 4 weeks of age until 13 weeks of age. During the course of the study, the body weight of the animals was measured twice-α-week for the whole study duration. At the end of the study, the mice were sacrificed and only tail samples were collected.

All animal experiments were performed as specified in the license authorized by the national Animal Experiment Board of Finland and according to the National Institutes of Health (Bethesda, MD, USA) guidelines for the care and use of laboratory animals. In total, 38 male R6/2 mice and 9 wild type (WT) littermates were used in the study. Only mice with normal plasma bile acid levels were used for the study.

Animals were housed at a standard temperature (22+1° C.) and in a light-controlled environment (lights on from 7 am to 8 pm) with ad libitum access to food and water.

Animals were grouped as follows:
Group 1: 9 male wild-type (WT) mice treated with vehicle (p.o.) from 4-13 weeks of age
Group 2: 9 male R6/2 mice treated with vehicle (p.o.) from 4-13 weeks of age
Group 3: 10 male R6/2 mice treated with (+)-α-DHTBZ (1.5 mg/kg, p.o.) from 4-13 weeks of age
Group 4: 10 male R6/2 mice treated with (+)-α-DHTBZ (3 mg/kg, p.o.) from 4-13 weeks of age Group 5: 9 male R6/2 mice treated with tetrabenazine (1.5 mg/kg, p.o.) from 4-13 weeks of age (+)-α-DHTBZ, TBZ and vehicle were administered each day (10 ml/kg, p.o., QD) at approximately the same time of the day for all the mice, starting at 9 a.m.-11 a.m., when the daily dosing was performed at least 1 hour before the tests.

Tremor Evaluation in the Tremor Monitor Chamber

The extent of tremor of the mice was evaluated at 7 and 13 weeks of age. The mice were brought to the experimental room for at least one hour prior to testing to acclimatise them. The mice were placed inside a Tremor Monitor (San Diego Instruments, SDI) chamber for a 10 minute acclimatisation period, following which the tremor activity of the mice was measured for approximately 8 minutes. The recorded frequencies (1-64 hertz) of activity and the number of tremor events were captured electronically.

Data were analysed by the Tremor Monitor software (San Diego Instruments) in a two part process. Using a Fast Fourier Transform (FFT), an output was provided showing the percentage of activity (energy) recorded at each frequency. A centre frequency of activity between 14-15 Hz was chosen, along with a bandwidth of 10 Hz. Using these parameters, tremor events were tabulated as short, long, and total events. A short event was an event that lasted 0.3-0.5 seconds and a long event lasted more than 0.5 seconds.

Figure 2:
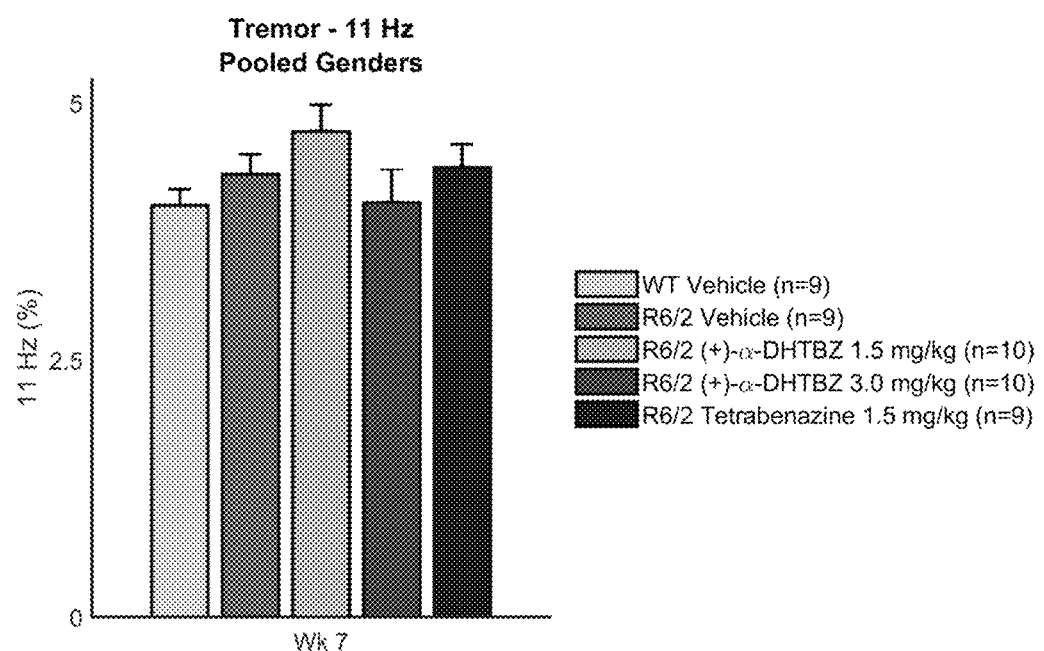
FIG. 2 shows the tremor power spectral density at 11 Hz of WT mice treated with vehicle and R6/2 mice treated with vehicle, (+)-α-DHTBZ 1.5 mg/kg, (+)-α-DHTBZ 3.0 mg/kg and TBZ 1.5 mg/kg.
Figure 3:
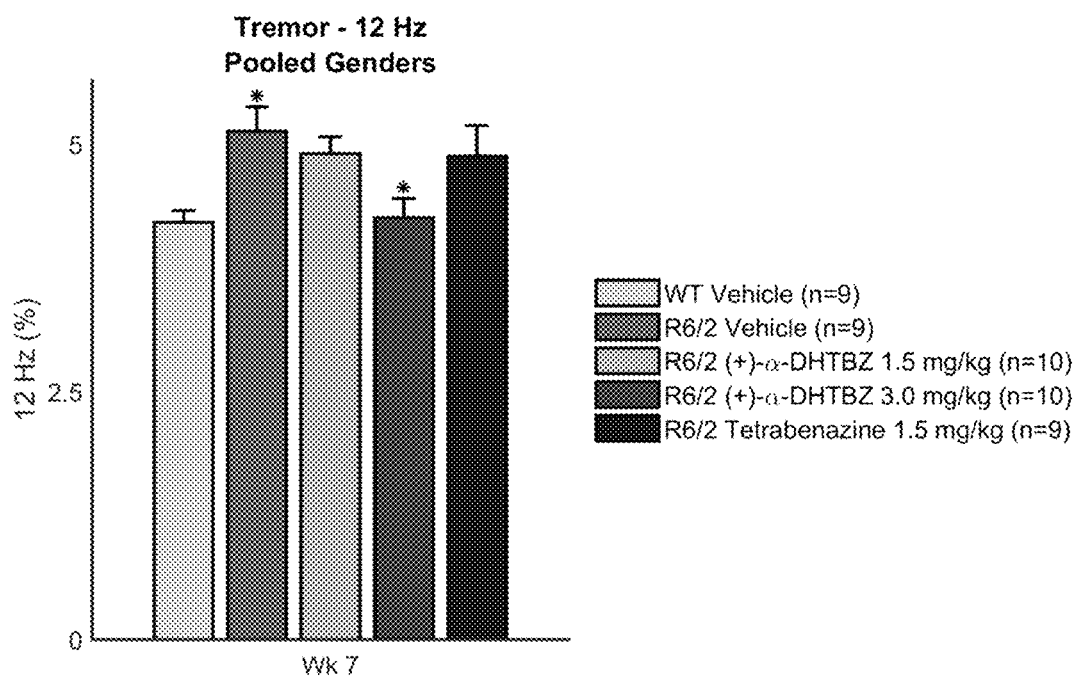
FIG. 3 shows the tremor power spectral density at 12 Hz of WT mice treated with vehicle and R6/2 mice treated with vehicle, (+)-α-DHTBZ 1.5 mg/kg, (+)-α-DHTBZ 3.0 mg/kg and TBZ 1.5 mg/kg.
Figure 4:
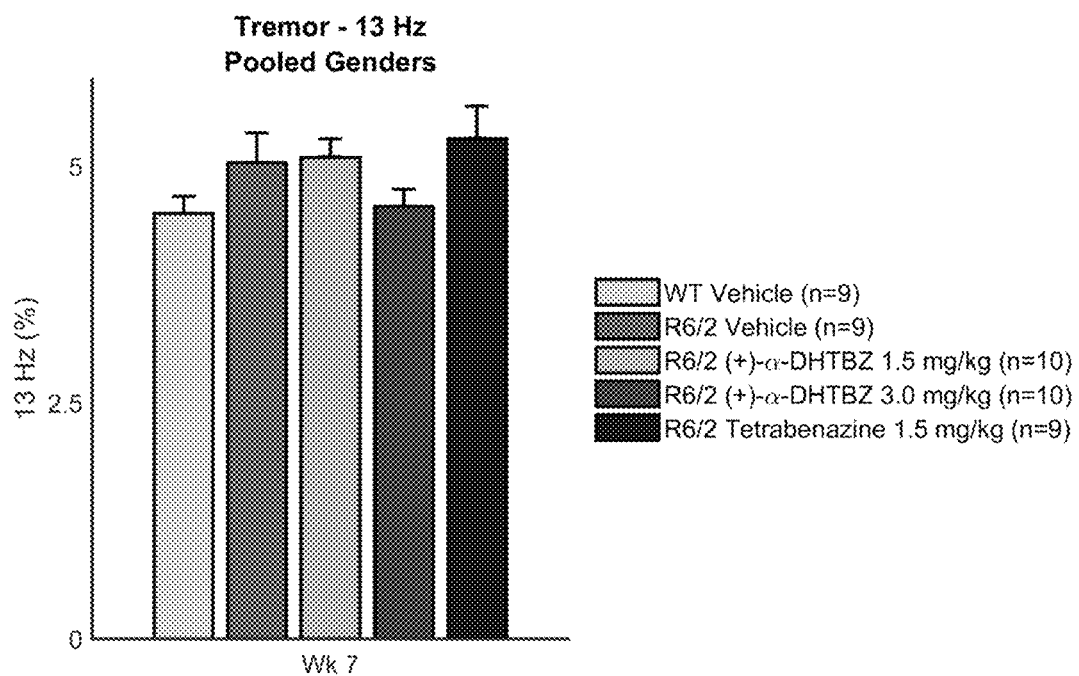
FIG. 4 shows the tremor power spectral density at 13 Hz of WT mice treated with vehicle and R6/2 mice treated with vehicle, (+)-α-DHTBZ 1.5 mg/kg, (+)-α-DHTBZ 3.0 mg/kg and TBZ 1.5 mg/kg.
Figure 5:
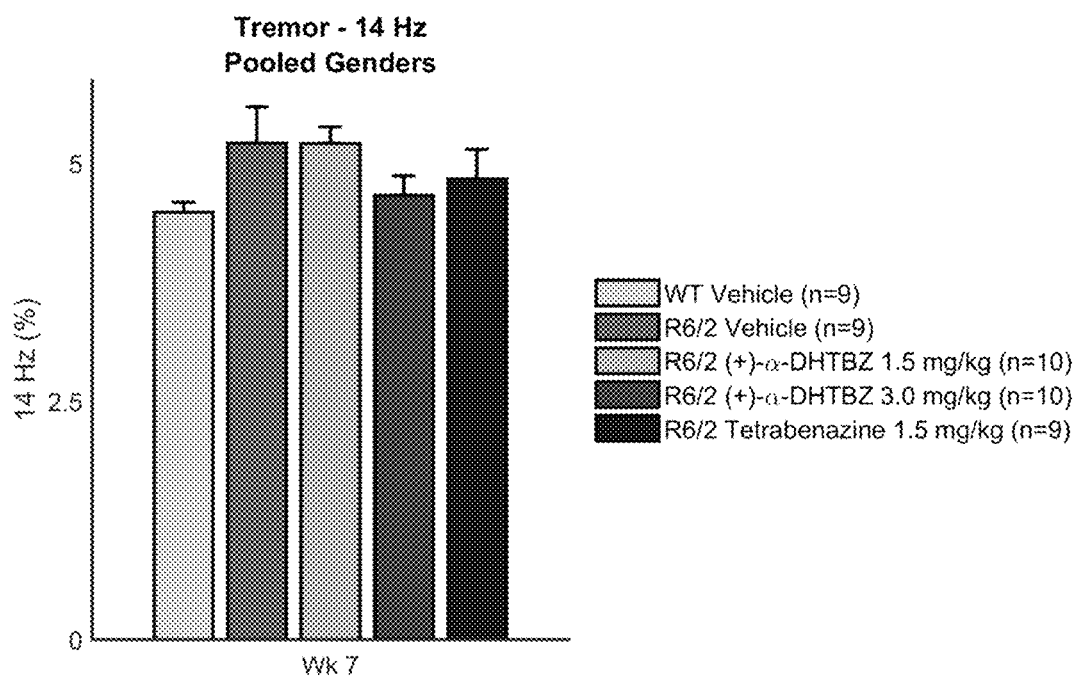
FIG. 5 shows the tremor power spectral density at 14 Hz of WT mice treated with vehicle and R6/2 mice treated with vehicle, (+)-α-DHTBZ 1.5 mg/kg, (+)-α-DHTBZ 3.0 mg/kg and TBZ 1.5 mg/kg.
Figure 6:
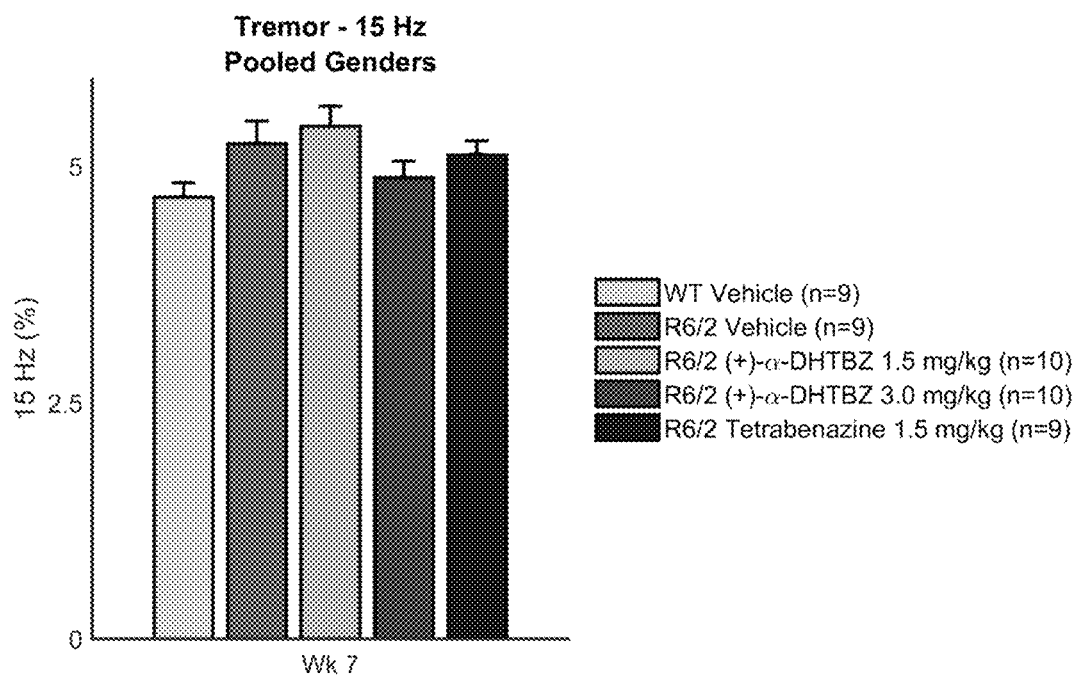
FIG. 6 shows the tremor power spectral density at 15 Hz of WT mice treated with vehicle and R6/2 mice treated with vehicle, (+)-α-DHTBZ 1.5 mg/kg, (+)-α-DHTBZ 3.0 mg/kg and TBZ 1.5 mg/kg.
Figure 7:
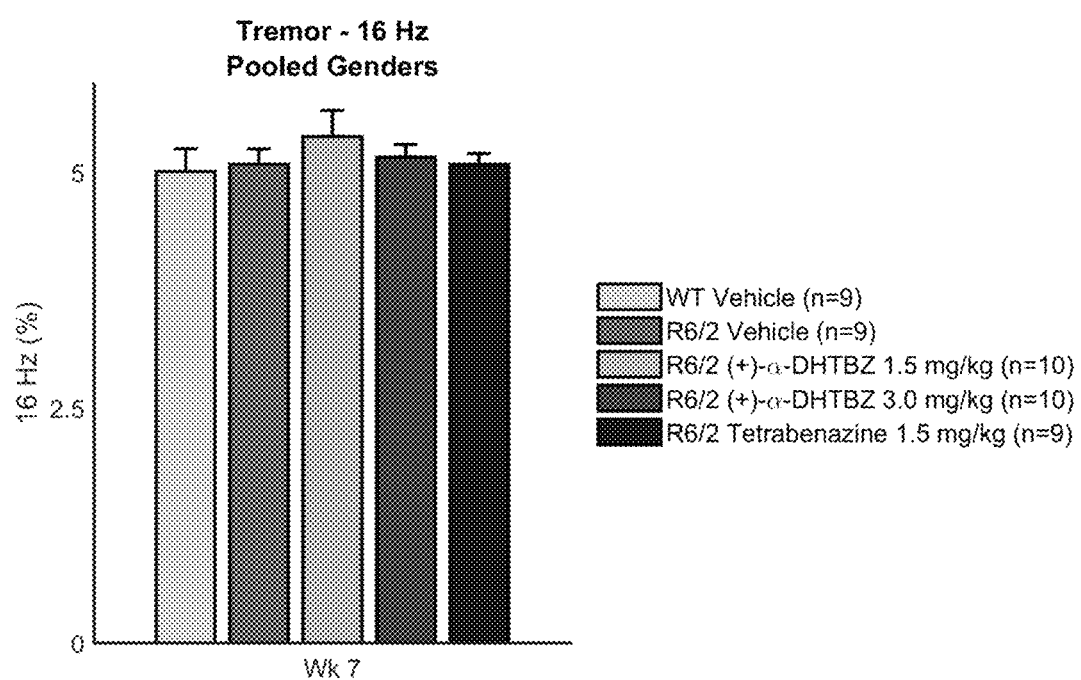
FIG. 7 shows the tremor power spectral density at 16 Hz of WT mice treated with vehicle and R6/2 mice treated with vehicle, (+)-α-DHTBZ 1.5 mg/kg, (+)-α-DHTBZ 3.0 mg/kg and TBZ 1.5 mg/kg.

The body tremor figures of vehicle treated WT and R6/2 mice as well as of (+)-α-DHTBZ- and tetrabenazine treated R6/2 mice at 7 and 13 weeks of age are presented in FIGS. 1 to 7.

FIGS. 1 to 7 show the power spectral density at tremors at 10 Hz, 11 Hz, 12 Hz, 13 Hz, 14 Hz, 15 Hz and 16 Hz respectively. Tremors at these frequencies are considered to be indicative of essential tremor.

Pairwise comparison t-test (assuming unequal variances) were used to determine significant differences between the test groups at each frequency. Significant differences were found and are marked for 12 Hz (see FIG. 3). For 12 Hz, the Tremor Power Spectral Density for the R6/2 Vehicle group was significantly different compared to WT mice, and results for the R6/2 (+)-α-DHTBZ 3.0 mg/kg group were significantly different compared to the R6/2 Vehicle group.

Survival Rates

In the case that the general health status of an animal was significantly worsened, the mouse was terminated by an overdose of $CO_2$, and decapitated. The mice were monitored until end point or the fulfilment of the euthanasia criteria.

The numbers of mice that did not die during the course of the study or that were not euthanised upon fulfilment of the above euthanasia criteria were recorded ("number of mice alive at the end of the study") and are shown in the table below.

| Group | Number of mice at the start of the study | Number of mice alive at the end of the study | Survival Rate (%) |
| --- | --- | --- | --- |
| Group 1 (Wild-type treated with vehicle) | 9 | 9 | 100 |
| Group 2 (R6/2 treated with vehicle) | 9 | 6 | 66.7 |
| Group 3 (R6/2 treated with (+)-DHTBZ, 1.5 mg/kg) | 10 | 10 | 100 |
| Group 4 (R6/2 treated with (+)-DHTBZ, 3.0 mg/kg) | 10 | 10 | 100 |
| Group 5 (R6/2 treated with TBZ, 1.5 mg/kg) | 9 | 7 | 77.8 |

A one-tailed, N-1 Two Proportion Test was used to determine statistically significant differences in the survival rates between the treatment groups. Survival rates were found to be significantly different for Groups 1 & 2, Groups 2 & 3 and Groups 2 & 4 (p values of 0.0289, 0.0233 and 0.0233 respectively).

Of the three non-surviving mice in Group 2, one died of seizure after dosing, one was euthanized due to its poor condition (it was almost completely immobile), and one was found dead.

Of the two non-surviving mice in Group 5, one was found dead and other died of seizure.

CONCLUSION (+)-α-Dihydrotetrabenazine has been shown to possess similar effects to tetrabenazine on reducing tremors in R6/2 mice. In addition, it has been shown that the survival rate of R6/2 mice treated with (+)-α-dihydrotetrabenazine (at both 1.5 mg/kg and 3.0 mg/kg) was significantly longer than the survival rates of the R6/2 mice treated with vehicle or tetrabenazine.

The results suggest that the (+)-α-dihydrotetrabenazine is providing more than just symptomatic relief and may be altering the course of the disease itself.

Equivalents

It will readily be apparent that numerous modifications and alterations may be made to the specific embodiments of the invention described above without departing from the principles underlying the invention. All such modifications and alterations are intended to be embraced by this application.

The invention claimed is:

1. A method of prolonging lifespan of a mammal having Huntington's Disease, the method comprising administering an effective amount of (+)-α-dihydrotetrabenazine or a pharmaceutically acceptable salt thereof to a mammalian subject in need thereof.

2. A method of prolonging lifespan of a mammal wherein the disease is:
   a) characterised by a mutation in the IT15 gene of the mammal;
   b) characterised by the presence of a mutated form of the Huntingtin protein; or
   c) caused by the presence of a mutated form of the Huntingtin protein, the method comprising administering an effective amount of (+)-α-dihydrotetrabenazine or a pharmaceutically acceptable salt thereof to a mammalian subject in need thereof.

3. A method according to claim 2 wherein the disease is characterised by a mutation in the IT15 gene of the mammal and wherein the mutation results in 36 or more CAG repeats in the IT15 gene.

4. A method according to claim 2 wherein the disease is characterised by the presence of a mutated form of the Huntingtin protein and wherein the mutated form of the Huntingtin protein results from the presence of 38 or greater CAG repeats on the IT-15 gene.

5. A method according to claim 1 wherein the mammalian subject is a human subject.

6. A method of reducing the life shortening effect of a disease in prolonging lifespan of a patient, the method comprising administering an effective amount of (+)-α-dihydrotetrabenazine or a pharmaceutically acceptable salt thereof to a patient who has been screened and has been determined as suffering from, or being at risk of suffering from, the disease, wherein the disease is characterised by the presence of 36 or greater CAG repeats on the IT-15 gene.

7. A method according to claim 1 wherein the method comprises administering to the mammalian subject (+)-α-dihydrotetrabenazine in an amount of from 1 mg to 500 mg.

8. A method according to claim 1 wherein the (+)-α-dihydrotetrabenazine has an isomeric purity of greater than 60%.

9. A method according to claim 1 wherein the (+)-α-dihydrotetrabenazine has an isomeric purity of greater than 95%.

10. A method according to claim 3 wherein the mutation results in 54 or more CAG repeats in the IT15 gene.

11. A method according to claim 4 wherein the mutated form of the Huntingtin protein results from the presence of 54 or greater CAG repeats on the IT-15 gene.

12. A method according to claim 6 wherein the disease is characterised by the presence of 54 or greater CAG repeats on the IT-15 gene.

* * * * *

UNITED STATES PATENT AND TRADEMARK OFFICE
CERTIFICATE OF CORRECTION

PATENT NO. : 12,042,493 B2
APPLICATION NO. : 17/054261
DATED : July 23, 2024
INVENTOR(S) : Duffield et al.

Page 1 of 1

It is certified that error appears in the above-identified patent and that said Letters Patent is hereby corrected as shown below:

In the Claims

Column 29, Lines 8-9: Claim 6, Delete "reducing the life shortening effect of a disease in"

Signed and Sealed this
First Day of October, 2024

*Katherine Kelly Vidal*

Katherine Kelly Vidal
*Director of the United States Patent and Trademark Office*